United States Patent [19]

Heath et al.

[11] Patent Number: 4,622,167

[45] Date of Patent: Nov. 11, 1986

[54] LOW VISCOSITY ALUMINUM HYDROXY CARBONATE GEL PROCESS

[75] Inventors: Wilbur G. Heath, Rehoboth Beach; Robert B. Casey, Milford, both of Del.

[73] Assignee: Barcroft Company, Lewes, Del.

[21] Appl. No.: 686,744

[22] Filed: Dec. 27, 1984

[51] Int. Cl.⁴ .................. B01J 13/00; A61K 33/10
[52] U.S. Cl. .......................... 252/315.7; 252/315.01; 422/188; 422/189; 424/156; 424/157
[58] Field of Search .............. 252/315.01, 315.7; 424/156, 157

[56] References Cited

U.S. PATENT DOCUMENTS

| | | | |
|---|---|---|---|
| 3,951,852 | 4/1976 | Gregory et al. | 424/156 X |
| 4,053,568 | 10/1977 | Madaus et al. | 424/157 X |
| 4,495,087 | 1/1985 | Ng et al. | 252/315.7 |
| 4,500,444 | 2/1985 | Beekman | 424/157 X |

*Primary Examiner*—Richard D. Lovering
*Attorney, Agent, or Firm*—James A. Nicholson; Alexis Barron; Martin F. Savitzky

[57] ABSTRACT

Process and system for the preparation of a low viscosity Aluminum Hydroxy Carbonate Gel having viscosity-resistant properties and a predetermined alkali ion content, comprising reacting under constant pH conditions an aqueous carbonate solution and an aqueous aluminum salt solution to form a reaction product, equilibrating the reaction product at naturally occurring pH and washing the equilibrated reaction product to provide the predetermined alkali ion content and the gel product by same processes.

21 Claims, 4 Drawing Figures

LOW VISCOSITY ALUMINUM HYDROXY CARBONATE GEL PROCESS

FIELD OF THE INVENTION

This invention relates to a process for the preparation of aluminum hydroxy carbonate gel of the type that is useful in the preparation of antacids, including orally administered preparations comprising one or more antacid materials.

Aluminum hydroxide carbonate gel is an aqueous suspension of aluminum hydroxide particles having carbonate anions adsorbed thereon as well as integrally complexed in the polymeric aluminum hydroxide structure. Aluminum hydroxide carbonate gels have been used as effective antacids either alone or in combination products which commonly include a magnesium compound as a second ingredient. Commercial suspension and tablet preparations which include a mixture of aluminum hydroxide and a magnesium compound are designed to offset the diarrheal effect of the magnesium compound with the constipating effect of aluminum hydroxide, and to provide an effective acid neutralizing capacity in a form which is easy to use and palatable to the user.

In the preparation of combination products including aluminum hydroxide carbonate gel and, in particular, in preparing aqueous combination suspensions, the properties of the individual antacid materials and their impact on the properties of the combination product must be carefully monitored to control the quality of the combination product. The properties of the gel which are of primary interest to the manufacturer of a combination product include its viscosity, its "mouth feel", its acid-neutralizing and -consuming capacity and its ability to blend predictably into the combination product. Other properties of concern to the manufacturer are the amount of impurities such as salt or alkali ion in the gel. In the production of antacids, it is desirable to reduce the content of salt impurities such as alkali salts, for example, sodium salts, in order to make these products more attractive to consumers who must or wish to restrict their salt intake and particularly their sodium intake. Accordingly, a product which includes little or no impurities such as alkali ion and which is relatively inexpensive to produce is desirable.

REPORTED DEVELOPMENTS

Aluminum hydroxy carbonate gels have been prepared by a number of processes which essentially involve reacting sodium aluminate with gaseous carbon dioxide or reacting aluminum chloride with sodium carbonate or reacting aluminum chloride with a mixture of sodium carbonate and sodium bicarbonate. Such processes are conducted at widely differing pH values, the pH variation of which is difficult to control in a commercial scale operation, and involve substantial washing of the aluminum hydroxide reaction product in order to lower the content of sodium ion to acceptable levels. The aluminum hydroxide gels obtained from such known processes exhibit viscosity properties which vary from lot to lot and which require the addition of viscosity modifiers in order to obtain a gel acceptable for use in the manufacture of a combination antacid.

An example of a process of the aforementioned type is disclosed in Canadian Pat. No. 1,154,932. This patent discloses the production of aluminum hydroxy carbonate gel by reacting aluminum chloride with an aqueous solution containing sodium carbonate and sodium bicarbonate. The process utilizes a dual-reactor system in which each reactor is maintained at low temperature and at an independent pH. The pH of the first reactor is disclosed as ranging from about 6.6 to about 7.0, while the pH of the second reactor is maintained at about 6.5. The patent discloses the preparation of a gel having a sodium ion content of 5 mg per gram of gel.

Another approach to the preparation of a low sodium-containing product is described in U.S. Pat. No. 4,105,579, which discloses a process using alkaline earth-containing reactants. This avoids the use of alkali ion-containing starting materials. This process, which is conducted at a pH of about 4.7 to about 5.5 produces an aluminum hydroxy carbonate gel having a very low sodium content, but a variable viscosity and alkaline earth ion content.

Studies of the physical properties of aluminum hydroxide gels have been reported. See, for example, J. R. Feldkamp, et al., "Effect of Adsorbed Carbonate on Surface Charge Characteristics and Physical Properties of Aluminum Hydroxide Gel", J. Pharm. Sci., Vol. 70, No. 6, 638, June 1981. The Feldkamp et al. study discloses that the gel particle of the aluminum hydroxide carbonate gels exhibits a net surface charge, and that the widely varying viscosities of many commercially available aluminum hydroxide gels can be modified by varying the gel pH. The term "net surface charge" may be defined as the sum of the positive and negative charges adsorbed on the surface of aluminum hydroxide gel particles. The sign and magnitude of the charges depend on the pH of the particle environment, the specific ions adsorbed on the particle surface and the ionic strength of the particle environment. The Feldkamp et al. study also discloses that such gels possess a characteristic property termed the zero point of charge (ZPC) which can be defined as the pH value where the net surface charge of the gel is measured as zero. In addition, Feldkamp et al. disclose that the gel viscosity may be changed by removing electrolytes with a water wash and that the viscosity of the gel is at its maximum value when its pH corresponds to the ZPC.

A comprehensive study of aluminum hydroxide carbonate gels is reported by Edward Carl Scholtz in his Ph.D. thesis, entitled, "Physiochemical Properties and Structural Aspects of Aluminum Hydroxy Carbonate Gels", Purdue University (December 1981). Scholtz discloses the laboratory preparation of aluminum hydroxy carbonate gels using a constant pH precipitation method wherein an aluminum salt is reacted with sodium carbonate and sodium bicarbonate in a single vessel batch process. Scholtz discloses the production of these gels at different pH and that the ZPC of the gels depend on the precipitation pH.

SUMMARY OF THE INVENTION

The present invention relates to a continuous process for the production of aluminum hydroxide carbonate gel having predetermined values of viscosity and alkali ion content and including particles having a predetermined net surface charge comprising:

(A) forming an acidic aqueous reaction mixture by combining continuously fed charges of an aqueous solution of alkali carbonate and an aqueous solution of aluminum salt;

(B) forming in said mixture a reaction product which includes aluminum hydroxide;

(C) continuously withdrawing from said mixture said product in an unequilibrated form;

(D) maintaining the pH of said reaction mixture at a predetermined value (±0.1) thereby producing a gel wherein said alkali ion content is correlated to said net surface charge; and (E) recovering from said withdrawn product said aluminum hydroxide gel.

Another aspect of the present invention relates to an improvement in a process of the type in which aluminum hydroxide carbonate gel, which includes particles of aluminum hydroxide, is continuously prepared by combining in a reaction mixture an aqueous solution of an alkali carbonate with an aqueous solution of an aluminum salt to form a reaction product, the improvement comprising providing a gel which has a predetermined alkali ion content and which includes particles having a predetermined net surface charge by maintaining said reaction mixture at a predetermined pH ±0.1 pH unit and equilibrating said reaction product under naturally occurring pH conditions.

The present invention also encompasses an aluminum hydroxy carbonate gel having viscosity change-resistant properties, that is, the change, if any, in the viscosity of the gel is no greater than about 50%, preferably no greater than about 30%, upon the addition thereto of an additive, such as potassium chloride, which changes the ionic strength of the gel. The viscosity change-resistant gel of the present invention can be utilized to prepare a combination antacid product, which includes said gel and magnesium hydroxide but does not include a viscosity modifier, and which exhibits a viscosity of less than about 1,000 cps. In accordance with the present invention, it is possible to produce a gel which possesses inherently viscosity change-resistant properties, that is, such properties being due solely to the chemical and physical makeup of the aluminum hydroxy carbonate particles at the predetermined sodium ion content of the gel. The addition to the gel of a viscosity modifier or additive is not necessary to achieve such property. Commercially available gels do not have inherently possessed, viscosity change-resistant properties and require the use of viscosity additives to stabilize the viscosity change that is normally encountered when the gel is utilized in the preparation of combination products which also include, for example, magnesium hydroxide gel. An aspect which underlies the development of the present invention comprises the recognition that the viscosity change-resistant properties of aluminum hydroxide carbonate gel prepared in accordance with the present invention are dependent on the alkali ion content of the gel and the pH of the initially formed reaction product.

A further aspect of the present invention relates to a system which can be used to produce a flowable aluminum hydroxide carbonate gel comprising:

reactor means for the containment of a reaction mixture prepared from an aqueous carbonate solution and an aqueous aluminum salt solution from which a reaction product is formed;

input means for the introduction of a charge of aqueous alkali carbonate solution into said reactor means;

output flow means for the withdrawal of said reaction product from said reactor means;

pH monitoring means for monitoring the pH of said withdrawn reaction product;

charge control means responsive to said pH monitoring means for varying the amount of the charge introduced into said reactor means thereby regulating the pH deviation of said reaction mixture;

equilibration means in which an equilibrated product is formed from said reaction product;

washing means for washing said equilibrated product with a washing liquid;

alkali monitoring means for monitoring the alkali content of said washed equilibrated product; and wash liquid, control means responsive to said alkali monitoring means for varying the amount of the liquid used to wash said equilibrated product, thereby regulating the alkali ion content of said flowable gel.

A number of advantages flow from the practice of the present invention which can be used to consistently and reliably produce an aluminum hydroxide carbonate gel having viscosity change-resistant properties and a predetermined alkali ion content. The gels of the present invention can be utilized in the preparation of combination products such as combination antacid suspensions without using viscosity additives to "fit" the gel viscosity to the requirements of the combination product. As discussed above, a disadvantage of commercially available gels is that their unpredictable viscosity behavior is a problematic factor when they are utilized in the preparation of combination products. In using such gels, each gel batch requires a custom viscosity modification comprising the addition of an additive, such as citric acid, in an amount which modifies the properties of the gel in a manner such that the gel does not effect an increase in the viscosity of the combination product beyond an acceptable level. The present invention provides a product which does not require the addition of a viscosity modifier and which inherently possesses the viscosity change-resistant properties desirable for the production of combination antacid products.

Another advantage of the present invention relates to the preparation of an aluminum hydroxide gel having a predetermined positive or negative net surface charge at any predetermined alkali ion content. Such a gel can be utilized in processes which require the gel to have a particle charge, such as processes requiring the use of dried aluminum hydroxide gel having either an electropositive or electronegative charge.

DETAILED DESCRIPTION

In the practice of the present invention, any suitable reactants can be used to form a reaction mixture which is capable of forming an aluminum hydroxy carbonate gel. Typically, the reaction mixture will be formed from an aqueous aluminum salt solution and an aqueous carbonate solution. The aluminum salt may be any aluminum halide such as, for example, aluminum chloride and aluminum bromide, or aluminum sulfate or aluminum nitrate, or a mixture thereof. The preferred aluminum salt is aluminum chloride. The carbonate solution may comprise an alkali carbonate such as, for example, sodium and potassium carbonate, the former being preferred. In a particularly preferred embodiment of the present invention, the aqueous carbonate solution comprises a mixture of alkali carbonate and alkali aluminate, most preferably a mixture of sodium carbonate and sodium aluminate.

The preferred reactants are combined preferably under conditions which are sufficient to produce an antacid-reactive gel and which minimize the production of unreactive aluminum compounds such as gibbsite. In order to minimize the production of such compounds, sodium aluminate comprises a minor ingredient of the carbonate solution. The preferred amount of sodium aluminate comprises up to about 3% w/w of the carbonate solution and, calculated as $Al_2O_3$, it comprises from 0 to about 1.5% w/w. The aluminate comprises about 0 to about 15% weight percent based on the carbonate in the aqueous solution and, most preferably, about 12 to about 14%.

The two reactant-containing solutions are brought together preferably under conditions such that each reactant does not intermingle prior to the substantial dispersal thereof in the reaction mixture. This enables the reaction mixture to be maintained at a substantially homogeneous pH without the formation of "hot" spots or widely fluctuating pH regions in the reaction mixture.

The pH conditions of the reaction mixture influence significantly the properties of the aluminum hydroxy carbonate gel product. The pH of the reaction mixture is maintained at a predetermined pH value and controlled within close tolerances. This can be accomplished by monitoring the pH of the reaction mixture or preferably by monitoring the pH of the reaction product as it is initially withdrawn from the reactor and by controlling the pH of this reaction product within ±0.1 pH unit, most preferably ±0.05 pH unit. Control of the pH can be accomplished by adjusting the relative amounts of the reactants introduced into the reaction mixture. In a preferred embodiment, the pH is controlled by adjusting the relative charge amounts of aqueous carbonate to aluminum salt solution, and in a most preferred embodiment, the control is effected by adjusting the flow rate of only the aqueous carbonate solution into the reaction mixture.

It is preferred to maintain the initially withdrawn reaction product at a predetermined pH which falls within the range of about 5.9 to about 6.1, and to control the predetermined pH within ±0.1 pH unit and most preferably ±0.05 pH unit.

The reaction can be conducted at any temperature which provides a fluid reaction medium and which is sufficient to produce the present gel. A preferred reaction temperature is from about 5° C. below ambient to about ambient, that is, from about 20° to about 30° C., and an exemplary reaction period is about 5 to about 30 minutes measured from the time reactants are introduced into the reaction mixture until they are removed from the reactant-containing environment in the form of reaction product. A reaction period of about 10 to about 30 min. has been used effectively. The preferred reaction pressure is atmospheric.

The continuous nature of the process of the present invention is such that the reaction mixture is replenished continuously with reactant(s) as reaction product is withdrawn continuously from the reactant-containing environment. The reaction mixture should be maintained in this environment for a sufficient period of time to enable the reactants to react substantially, but not to the extent of forming a heterogeneous mixture which includes a precipitate. The reaction product withdrawn from the reaction mixture is substantially homogeneous and comprises a mixture of aqueous alkali salt, aluminum hydroxide, dissolved carbon dioxide and minor amounts of starting materials in a dynamic equilibrium. In this environment, aluminum hydroxy carbonate gel particles are forming and growing in size, as carbon dioxide is being released and the concentration of starting materials is diminishing rapidly.

The withdrawn reaction product is subjected to equilibrium conditions for a time sufficient to form a stable heterogeneous suspension or colloidal dispersion of aluminum hydroxy carbonate gel particles. This can be done conveniently at ambient temperature, typically room temperature, that is, about 20° to about 30° C., and at atmospheric pressure. Although the equilibrating time can vary over a wide range, depending on a number of factors, good results have been obtained in less than about four and even less than about three hours. Equilibration is conducted under conditions in which the pH is allowed to vary naturally, that is, the pH of the equilibrating product is permitted to fluctuate under conditions such that any additional reaction is attributed only to that which occurs due to the addition of the withdrawn reaction product to the equilibrating product. In a preferred embodiment, the pH of the equilibrating product naturally rises due to the evolution and release of non-adsorbed carbon dioxide.

After the reaction product is equilibrated, the aluminum hydroxide carbonate gel precipitate is separated from the aqueous suspension, for example, by filtering, and the residual alkali content of the precipitate is adjusted to the desired level by washing under controlled conditions. The washing conditions may be modified by increasing or decreasing the washing time, the washing temperature or the size of the washing zone. The washed precipitate can then be dewatered and blended to form a pumpable gel. The amount of impurities, such as chloride and alkali ion, in the pumpable gel can be controlled by modifying the washing conditions in response to any detected changes in the gel's impurities' level. Changes in the level of impurities can be detected by measuring properties of the gel such as its conductivity properties.

The alkali ion content of the pumpable gel can be controlled by the present process within a range of about ±0.08 mg of alkali ion per gram of gel product and most preferably within a range of about ±0.03 mg per gram of gel.

The process of the present invention can be used to produce a gel which has precise alkali ion content and which includes particles having a net surface charge, the sign and magnitude of which is a function of the closely controlled pH conditions of the reaction mixture and the washing conditions. As the equilibrated reaction product is washed, its alkali ion content approaches a specific value, which can be predetermined as described above, the net surface charge of the gel particles approach the ZPC, and the washed product develops viscosity change-resistant properties. For example, washing the reaction product with deionized water results in lowering the alkali content thereof as the net surface charge and ZPC of the gel particles are modified also. As washing continues, the viscosity change-resistant properties of the product develop and are at its maximum when the net surface charge and the ZPC of the gel particles coincide. A viscosity change-resistant gel having a predetermined alkali ion content of about 0.15 to about 0.50 mg/g can be produced by controlling the pH of the reaction mixture and the washing of the equilibrated reaction product. A preferred embodiment of the present invention comprises a viscosity change-resistant gel having an alkali ion content of about 0.18 to about 0.25 mg/g of gel.

Another aspect of this invention relates to the preparation of a gel which has a net positive or negative surface charge and which is useful in the preparation of products such as a dried gel requiring a surface charge.

Figure 1:
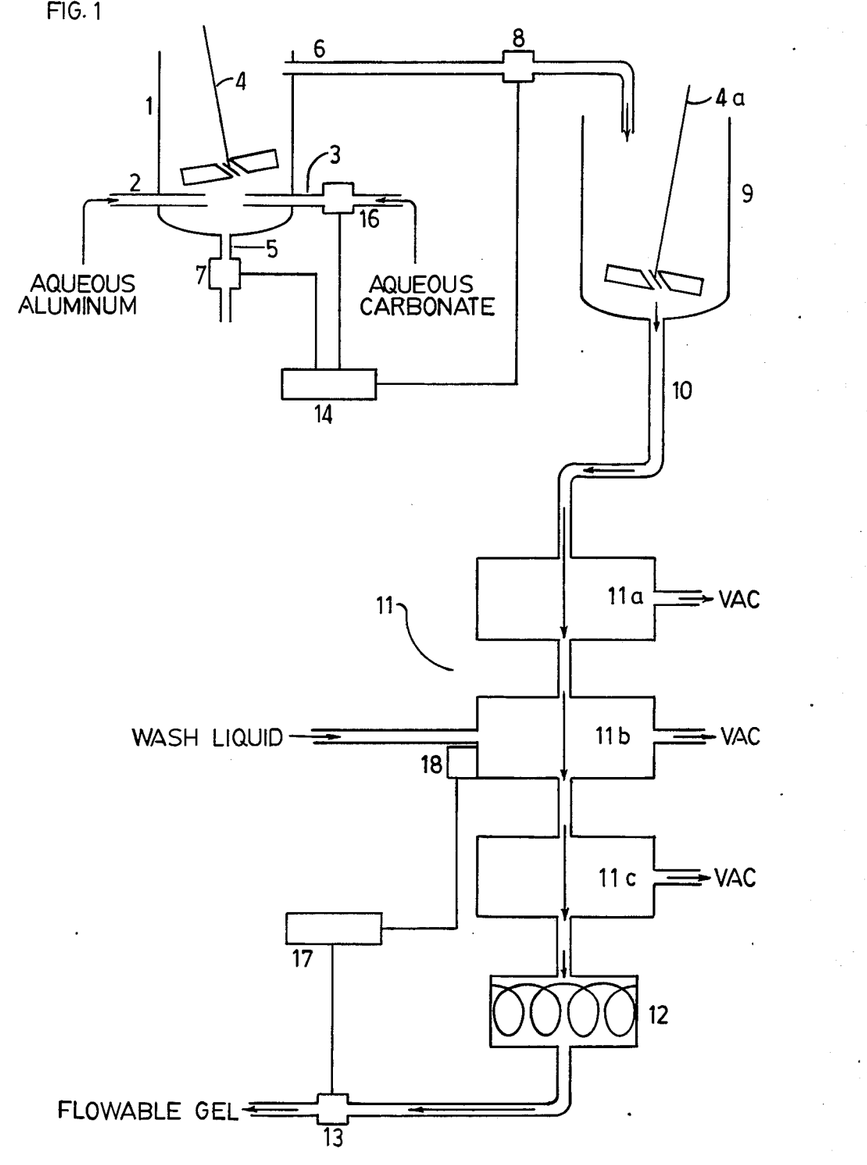
FIG. 1 depicts schematically an embodiment of the present system for the continuous production of aluminum hydroxide carbonate gel.
Figure 2:
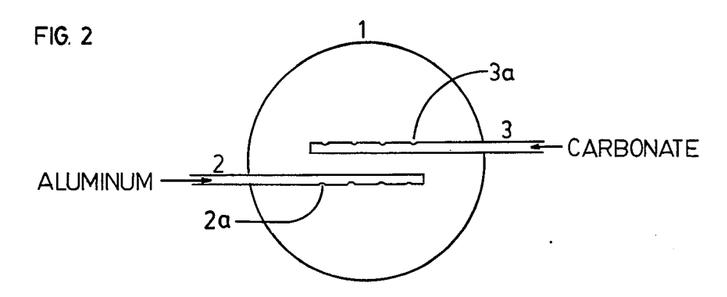
FIG. 2 depicts a schematic downward view of the reactor inlet system within the reactor of FIG. 1.
Figure 3:
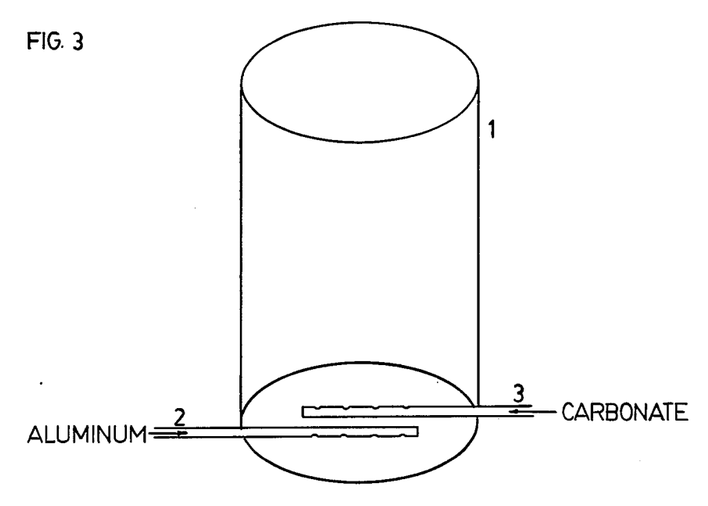
FIG. 3 depicts a perspective view of the reactor of FIG. 1.

A preferred embodiment of the present invention is described with reference to the accompanying drawings as shown in FIG. 1, a reactor vessel 1 has inlets 2 and 3 for the introduction of an aqueous carbonate solution and an aqueous aluminum salt solution respectively. In a preferred form, the inlets are arranged as illustrated in FIGS. 2 and 3 wherein the inlet openings 2a and 3a for the introduction of each reactant are arranged diametrically opposite one another within the reaction vessel. The reactor vessel 1 is provided with a conventional form of stirrer 4 which functions to agitate the contents of the reactor vessel 1 while imparting low shear with high mass transfer. The bottom of the reactor vessel 1 is provided with a sample outlet 5 and the upper portion of the reactor vessel 1 is provided with a reaction mixture output flow line 6. pH monitors 7 and 8 are located respectively in the sample outlet 5 and in the output flow line 6. The output flow line 6 empties into the equilibration vessel 9 which is also equipped with a conventional form of stirrer 4a and an outlet line 10 which leads to the forming zone 11a of the vacuum filter 11. The vacuum filter 11 comprises three zones, including the forming zone 11a, the washing zone 11b, and the drying zone 11c, each of which is vacuum equipped to withdraw liquids. The gel precipitate and the liquid phase of the equilibrated reaction product are separated in the forming zone 11a, and the gel precipitate is transferred to the washing zone 11b, where it is washed, and then to the drying zone 11c, where excess washing liquid is removed. The dewatered and washed gel precipitate is removed from the filter 11 and treated in ribbon blender 12 which converts it into a pumpable gel. The pumpable gel is pumped past an alkali ion monitor 13 which measures the conductivity of the gel.

A logic circuit 14 is associated with the pH monitors 7 and 8 and the charge control means 16 and functions to control the pH of the reaction mixture in response to pH variations of ±0.1 pH unit measured by the pH monitors 7 and 8. At start up, pH monitor 7 monitors the reaction mixture, but as the process continues, and a flow of reaction product passes pH monitor 8, the pH measured at monitor 8 controls the pH of the reaction mixture.

A logic circuit 17 is associated with the washing control means 18 and the ion monitor 13 and functions to control the extent of washing of the gel precipitate to produce a gel having a predetermined alkali ion content.

Figure 4:
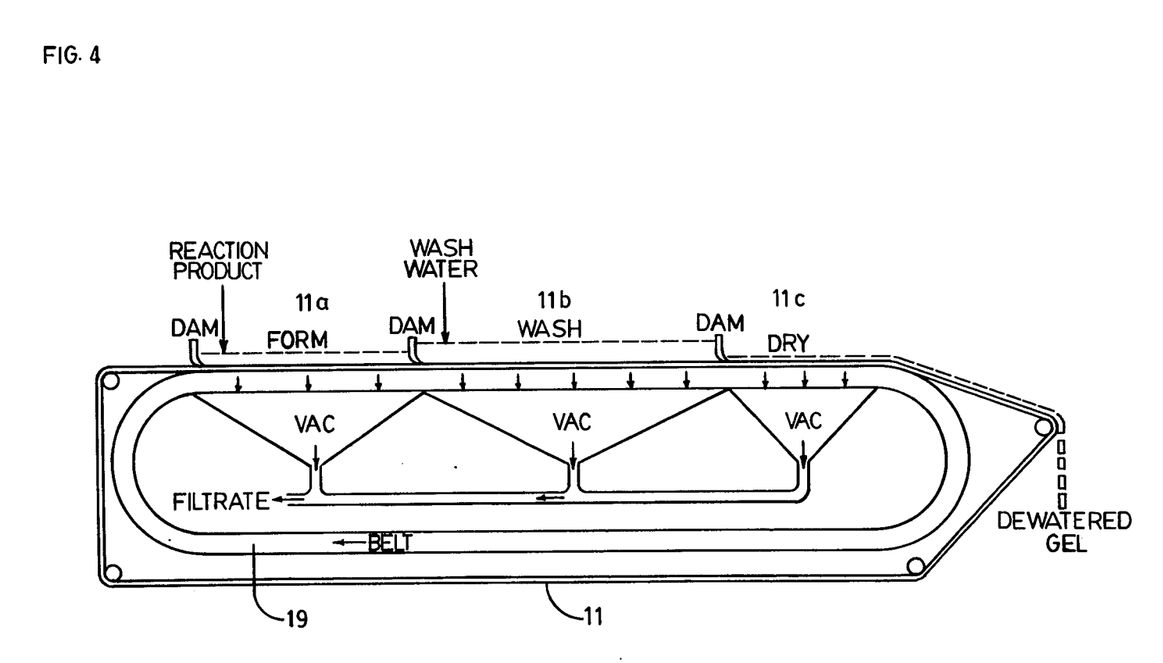
FIG. 4 depicts schematically a horizontal belt vacuum filter useful in the practice of the present invention.

The preferred device for separating the gel precipitate from the liquid phase of the equilibrated reaction product is a horizontal belt vacuum filter 11 which is schematically depicted in FIG. 4. There are a number of advantages associated with the use of this type of filter. In the preferred embodiment of the invention, the filter 11 is associated with the alkali ion control system comprising the ion monitor 13, the washing control means 18, and the logic circuit 17, and provides the ability to control the alkali ion content of the gel while maintaining a constant gel production rate. More particularly, the horizontal belt vacuum filter 11 functions to receive a constant flow of equilibrated reaction product onto its forming zone 11a and to process the deposited reaction product at variable speeds, the latter being accomplished by changing the speed of the horizontal conveyor belt 19. This capability can be used to produce at a constant rate gel which can be subjected to varying washing times. This is accomplished because a change in the horizontal belt speed changes the washing time of the gel precipitate, and the thickness of the gel precipitate layer being washed, resulting in a constant gel production rate.

In a preferred embodiment, a filter feed tank, not shown, is interposed between the equilibration vessel 9 and the forming zone 11a of the vacuum filter 11. The tank functions as a further equilibration environment and as a storage vessel in the event that equipment down line is shutdown in the middle of a process run.

The preferred embodiment also utilizes a colloid mill and a homogenizer, which are not shown, and which induce shear into the gel thereby modifying its viscosity to a desired value. In the most preferred embodiment, bacterial contamination of the final product is controlled by utilizing highly chlorinated wash water which contains about 20 to about 100 ppm of chlorine. It is also preferred to utilize a heat exchanger to inhibit deterioration of the product by reducing the temperature of the gel prior to the homogenization step.

In order to avoid introducing into the gel external metallic contaminates such as ferric or ferrous ions, apparatus used in the production process is fabricated preferably from non-metallic containing materials such as fiberglass/resin materials. It is preferred that the input flow lines, the reactor, the output flow lines, the equilibration vessel and the filter feed vessel be fabricated from such non-metallic containing materials. It is also preferred that the tanks and mixing apparatus in which the aqueous aluminum and aqueous carbonate solutions are prepared comprise non-metallic materials.

A most preferred embodiment of the present process and system utilizes a computer control system which monitors and controls each and every aspect of the present process including the reaction mixture pH and alkali ion content of the gel. The preferred computer control system is the Fisher ® PRoVOX ® Batch Control System.

EXAMPLE

The following is a description of a preferred embodiment of the present invention.

The process is initiated by pumping simultaneously an aqueous solution of aluminum chloride (9.5% w/w) at a flow rate of about 6.9 gal. per min. (gpm) and an aqueous solution of sodium carbonate (9% w/w) and $Na_2Al_2O_4$ (1.25% w/w as "$Al_2O_3$") at a rate of about 8 gpm into a reactor vessel 1 (445 gal. working capacity) which is substantially filled with water. The reactor vessel contents are stirred at ambient temperature and atmospheric pressure, while the pH thereof is monitored by a pH probe 7 located in sample line 5 and controlled to maintain a reactor contents pH of 6.05 by adjusting the aqueous carbonate flow rate. As reactor contents empty into output flow line 6, the pH of the withdrawn reaction product is monitored and the carbonate solution flow rate into the reactor vessel 1 is adjusted to maintain the pH of the reaction mixture at 6.05±0.10.

The output flow line 6 empties into the equilibration vessel 9, the contents of which are stirred and maintained at ambient temperature and which is filled to a capacity of about 855 gal. The contents of the equilibration vessel 9 resides therein for about 45–50 minutes, after which it is pumped into a filter feed tank, not shown in FIG. 1.

The contents of the filter feed tank are also stirred and maintained at ambient temperature and the tank is filled to a capacity of about 1830 gal. before its contents are pumped at a rate of about 15 gpm onto the forming zone 11a of a horizontal belt vacuum filter 11, which is set to convey the equilibrated reaction product through the filter separation process at an initial belt speed of about 5.5 ft/min. The equilibrated reaction product is separated into a gel precipitate and a reaction filtrate by vacuum filtration (468 mm Hg) forming a gel filter cake which is transferred by the conveyor belt to the washing zone 11b where it is flooded with wash water maintained at about 103° F. The flooded filter cake is continuously subjected to vacuum (533 mm Hg) which separates the wash water from the gel filter cake, and is transferred to the vacuum drying zone 11c (533 mm Hg) where excess water is removed. The resulting dewatered gel filter cake (viscosity of about 100,000 cps) is separated from the conveyor belt and transferred to a ribbon blender 12 which converts the dewatered gel filter cake to a pumpable gel by reducing its viscosity to about 60,000 cps. The gel's viscosity is reduced further by treatment with a colloid mill and a homogenizer, not shown in FIG. 1.

The sodium ion content of the low viscosity gel is controlled by monitoring the conductivity of the flow of milled gel at the ion monitor 13 and adjusting the vacuum filter belt speed, which modifies the washing time of the gel filter cake, in response to variations in the gel's conductivity. The gel conductivity is controlled at about 400 $\mu$mhos. The final product has a viscosity of 435 cps measured by a Brookfield LVT using spindle No. 2 at 12 rpm (adjusted to 8.5% $Al_2O_3$), contains 0.21 mg/g of sodium (at 8.5% $Al_2O_3$) and assays as 9.35% $Al_2O_3$.

Table I below presents a description of the properties of the aluminum hydroxide gel obtained according to the preceding example and those of gels produced by three additional process runs according to the present invention. The information presented in Table I includes the aluminum oxide concentration, the sodium concentration and the viscosity and viscosity-change properties of four separate gels prepared by the present process. The aluminum oxide concentration is indicated as a percent value based on the total weight of the gel. The remaining information is presented on a standardized basis in which the gel is diluted to a standard 8.5% concentration (w/w). The viscosity measurements are made using a Brookfield model LVT equipped with a No. 2 spindle run at 12 rpm. In addition to the viscosity of a standardized gel (8.5% $Al_2O_3$), Table I presents the viscosity values of the following mixtures: a mixture of a standardized gel plus 26 mg/g of KCl; a mixture of a standardized gel plus citric acid (300 mg of anhydrous citric acid to 175 g of standardized gel); and two combination antacid products including the standardized gel. The combination product labeled as "CP1" includes 600 mg $Mg(OH)_2$, 6 g of standardized gel, 0.075% w/v of a gum, and 0.12% w/v of citric acid per 10 ml of aqueous suspension (the gum is present in the formulation for the purpose of modifying the "mouth feel" of the formulation and only incidentally increases the viscosity of the aqueous suspension by an amount of about 120–160 cps). The combination product labeled as "CP2" presents the viscosity of the combination product excluding the citric acid ingredient.

TABLE I

| Aluminum Hydroxide Carbonate Gel Process Run | % $Al_2O_3$ | Na Conc. in gel at 8.5% $Al_2O_3$ mg/g | Viscosity (cps) @8.5% | +KCl | +cit acid | CP1 | CP2 |
|---|---|---|---|---|---|---|---|
| 1 (above example) | 9.35 | 0.21 | 435 | 563 | 63 | 500 | 578 |
| 2 | 9.92 | 0.17 | 328 | 413 | 50 | 388 | 850 |
| 3 | 10.00 | 0.21 | 413 | 383 | 145 | 588 | 856* |
| 4 | 9.64 | 0.25 | 418 | 483 | 103 | 530 | 660 |

*approximated value

The approximated viscosity value of "CP2" for process run 3 is calculated by adding the viscosity loss of the gel in the presence of citric acid to the viscosity of the combination product "CP1".

Table I shows that the viscosities of the gels produced in accordance with the present invention change very little when the ionic strength thereof is changed by the addition of potassium chloride (KCl). The substantial equivalence of the viscosity values of the standardized gel and the KCl containing gels shown in Table I is indicative of the viscosity change-resistant properties of the present gels.

The viscosity values for combination products "CP1" and "CP2" show that a combination product having a viscosity of less than 1,000 cps can be prepared using the present gels without including the viscosity modifier, citric acid. As will be shown in Table II below, commercially available gels require the presence of a viscosity modifier in order to obtain a combination product with an acceptable viscosity of less than 1,000 cps.

Comparative data relating to the viscosity variability of a number of different commercially available aluminum hydroxide carbonate gels is shown in Table II below. The viscosity of the gel is presented in the following forms: "As is", that is, prior to standardization to constant aluminum oxide concentration; at a standardized concentration of 8.5% $Al_2O_3$; the standardized concentration plus citric acid; and, as two combination antacid products.

TABLE II

| Viscosity of Commercial Aluminum Hydroxy Carbonate Gels | | | | | |
|---|---|---|---|---|---|
| Lot No. | "As Is" | @8.5% | +cit acid | CP1 | CP2* |
| 5 | 2407 | 1632 | 32 | 842 | 2442 |
| 6 | 2047 | 1052 | 12 | 907 | 1947 |
| 7 | 1392 | 495 | 340 | 1785 | 1940 |

TABLE II-continued

| Viscosity of Commercial Aluminum Hydroxy Carbonate Gels | | | | |
|---|---|---|---|---|
| Lot No. | "As Is" | @8.5% | +cit acid | CP1 | CP2* |
| 8 | 1767 | 882 | 5 | 607 | 1484 |
| 9 | 1690 | 770 | 25 | 575 | 1320 |
| 10 | 1400 | 785 | 7 | 870 | 1648 |
| 11 | 1295 | 990 | 52 | 727 | 1665 |
| 12 | 1987 | 1317 | 57 | 1075 | 2335 |
| 13 | 800 | 512 | 1027 | 2500 | 1985 |

*approximated value

In Table II, the viscosity of the combination products, CP1, which include the commercial gels, except for the products prepared from gel lots 7, 12 and 13, are below 1000 cps. The low viscosity values for these products are the result of the presence of citric acid. Citric acid is required in order to achieve an acceptable viscosity level of less than 1000 cps. A comparison of the information in the colum labeled "+cit acid" and the viscosity of the commercial gels (at @8.5%) shows clearly the impact that citric acid has on commercial gel viscosity. The viscosity change effected by the citric acid in the commercial gels is substantial and the impact of the exclusion of citric acid on the viscosity of the combination product is shown clearly by the viscosity values presented in the column labeled "CP2*". The exclusion of citric acid from the combination product would result in a product viscosity in substantial excess of 1000 cps. In contrast, as shown in Table I above, the gels of the present invention can be used to prepare the combination product without the use of citric acid.

It should be noted that the citric acid in the combination product functions not only as a viscosity modifier but also impacts adversely on the acid-neutralizing and -consuming capacity of the combination product. It not only reduces the overall amount of antacid available for acid neutralization but also reduces the rate of acid neutralization. Furthermore, the elimination of citric acid from the combination product formulation is desirable not only to increase the antacid effectiveness of the combination product but also to avoid the necessity of determining the amount of citric acid required to bring the viscosity of the presently available aluminum hydroxide gel product to a level which is acceptable for use in the combination formulation.

Preferred aluminum hydroxide carbonate gels prepared by the present process exhibit an acid consuming capacity of not less than about 22.5 ml of 0.1 N HCl per 0.5 g of gel, a preferred sodium ion content of about 0.19 to about 0.25 mg/g and a preferred viscosity of about 200 to about 800 cps (8.5% $Al_2O_3$) measured by a Brookfield LVT viscometer equipped with spindle No. 2 at 12 rpm.

We claim:

1. A continuous process for the production of aluminum hydroxide carbonate gel having predetermined values of viscosity and alkali ion content and including particles having a predetermined net surface charge comprising:
   (A) forming an acidic aqueous reaction mixture by combining continuously fed charges of an aqueous solution of alkali carbonate and an aqueous solution of aluminum salt;
   (B) forming in said mixture a reaction product which includes aluminum hydroxide wherein the pH of said mixture containing said aluminum hydroxide tends to vary;
   (C) maintaining the pH of said reaction mixture at a predetermined value ($\pm 0.1$) thereby producing a gel wherein said alkali ion content is correlated to said net surface charge;
   (D) continuously withdrawing from said mixture said product in an unequilibrated form;
   (E) forming an equilibrated product by equilibrating said withdrawn product under naturally occurring pH conditions; and
   (F) recovering from said equilibrated product said aluminum hydroxide gel.

2. A process according to claim 1 wherein said continuously fed charges are introduced into said reaction mixture such that each of said charges do not intermingle prior to the substantial dispersal thereof in said reaction mixture.

3. A process according to claim 2 wherein said unequilibrated reaction product resides in said reaction mixture for about 5 to about 30 min. and is maintained at ambient temperature.

4. A process according to claim 3 wherein said pH is maintained by controlling the amount of said charged carbonate and/or said aluminum salt fed to said mixture.

5. A process according to claim 1 wherein said reaction mixture pH is maintained by maintaining the pH of said unequilibrated product at a predetermined value ($\pm 0.1$).

6. A process according to claim 1 including washing said equilibrated product and regulating the alkali ion content of said equilibrated product within a range of about $\pm 0.08$ mg of alkali ion per gram of said gel by monitoring said alkali ion content and controlling the extent of said washing.

7. A process according to claim 6 wherein said gel is formed by vacuum drying and blending said washed product.

8. A process according to claim 7 wherein said alkali ion content is controlled at a constant production rate of said gel.

9. A process according to claim 8 wherein said reaction mixture pH is maintained at a value from about 5.9 to about 6.1 ($\pm$ about 0.05).

10. A process according to claim 1 wherein said equilibrated reaction product is formed at ambient temperature.

11. A process according to claim 10 wherein said equilibrated reaction product is formed under conditions wherein further reaction occurring in said unequilibrated product is attributed to said unequilibrated product withdrawn from said reaction mixture.

12. A method for the preparation of dried aluminum hydroxide gel having a predetermined net surface charge comprising drying aluminum hydroxide carbonate gel prepared by the process of claim 1 and recovering said dried gel.

13. In a continuous process for the preparation of an aluminum hydroxide carbonate gel comprising combining in a reaction mixture an aqueous solution of alkali carbonate with an aqueous solution of an aluminum salt to form a reaction product including particles comprising aluminum hydroxide, and wherein the pH of said mixture containing said products tends to very, the improvement comprising providing a gel which includes particles having a predetermined net surface charge and which has a predetermined alkali content by maintaining said reaction mixture at a predetermined pH $\pm 0.05$ pH unit and equilibrating said reaction product under naturally occurring pH conditions.

14. A process for the continuous production of an aluminum hydroxide carbonate flowable gel having viscosity change-resistant properties, a viscosity of about 200 to about 800 cps and a sodium content of about 0.19 to about 0.25 mg/g comprising:

continuously feeding into an agitated reaction mixture an input charge of an aqueous containing sodium carbonate and sodium aluminate solution and an input charge of an aqueous aluminum salt solution;

forming in said mixture an unequilibrated reaction product including particles of aluminum hydroxide, said product-containing mixture tending to vary in pH;

withdrawing an output stream of said reaction product from said reaction mixture;

allowing said withdrawn reaction product to equilibrate to a stable pH to form an equilibrated reaction product including sodium ions and an aluminum hydroxide gel precipitate;

washing said precipitate to achieve the abovesaid sodium content;

inducing sufficient shear into said washed precipitate to form said flowable gel;

wherein said viscosity change-resistant properties of said flowable gel are provided by maintaining said output stream of unequilibrated reaction product at a pH of about 6±0.1.

15. A process according to claim 14 wherein said reaction mixture and said withdrawn reaction product are maintained at ambient temperature.

16. A continuous process for the production of aluminum hydroxide carbonate gel comprising:
(A) forming an acidic aqueous reaction mixture by combining continuously fed charges of an aqueous solution of alkali carbonate and an aqueous solution of aluminum salt;
(B) forming in said mixture a reaction product which includes aluminum hydroxide;
(C) maintaining the pH of said reaction mixture at a predetermined value (±0.1) by adjusting the relative amounts of the charges fed to said reaction mixture;
(D) continuously withdrawing from said mixture said product in an unequilibrated form;
(E) subjecting said withdrawn product in unequilibrated form to equilibrating conditions under which the pH thereof is allowed to vary naturally and in which recoverable aluminum hydroxide carbonate gel particles are formed; and
(F) recovering from said withdrawn and equilibrated product said aluminum hydroxide carbonate gel particles.

17. A process according to claim 16 wherein the pH of said withdrawn product which is subjected to said equilibrating conditions naturally rises.

18. A process according to claim 16 wherein said pH is maintained by adjusting the flow rate of only said carbonate solution.

19. A process according to claim 16 wherein said pH is maintained within the range of about 5.9 to about 6.1.

20. A process according to claim 19 wherein the pH of said withdrawn product which is subjected to said equilibrating conditions naturally rises to a value which is above that at which the pH is maintained.

21. A process according to claim 16, 17, 18, 19, or 20 wherein said pH is maintained at a value within ±0.05 pH unit.

* * * * *